United States Patent [19]

Mazza et al.

[11] Patent Number: 4,815,978

[45] Date of Patent: Mar. 28, 1989

[54] CLINICAL ANALYSIS METHODS AND SYSTEMS

[75] Inventors: John C. Mazza, El Toro; Robert R. Thompson, Orange, both of Calif.

[73] Assignee: Baxter Travenol Laboratories, Inc., Deerfield, Ill.

[21] Appl. No.: 858,366

[22] Filed: Apr. 30, 1986

[51] Int. Cl.$^4$ .......................... C12Q 1/00; C12M 1/34; C12M 1/04; C12M 1/02
[52] U.S. Cl. ....................................... 435/4; 435/291; 435/313; 435/316; 366/101; 261/119.1; 422/63; 422/100
[58] Field of Search .................. 435/4, 296, 291, 313, 435/315, 316; 422/63, 64, 65, 66, 67, 68, 99, 100, 102; 366/101, 106, 107; 436/47; 261/119.1

[56] References Cited

U.S. PATENT DOCUMENTS

| | | | |
|---|---|---|---|
| 2,990,339 | 6/1961 | Frank et al. | 435/316 X |
| 3,398,935 | 8/1968 | Livesay et al. | 366/101 |
| 3,405,920 | 10/1968 | Lefrancois | 435/313 X |
| 3,607,659 | 9/1971 | Bloomer | 435/313 X |
| 4,286,637 | 9/1981 | Wilson | 422/57 X |
| 4,325,910 | 4/1982 | Jordan | 422/65 X |
| 4,338,279 | 7/1982 | Orimo et al. | 422/65 X |
| 4,528,159 | 7/1985 | Liston | 422/65 |

FOREIGN PATENT DOCUMENTS

WO85/0357 1/1985 PCT Int'l Appl. .

OTHER PUBLICATIONS

Product brochure: "This is Paramax, The Paramax Analytical System", American Dade, Division of American Hospital Supply Corporation, Miami, Fla., distributed by American Scientific Products, Division of American Hospital Supply Corporation, McGraw Park, Ill., published before Jun. 20, 1983, 12 pages.

*Primary Examiner*—Robert J. Warden
*Assistant Examiner*—Randall E. Deck
*Attorney, Agent, or Firm*—Marjorie D. Hunter; Paul C. Flattery; Susan B. Fentress

[57] ABSTRACT

An improved and unique mixing technique particularly useful as part of the process for the clinical analysis of liquid biological samples is described. The sample is placed in a cuvette along with a reagent and a diluent. The top (opening) of the cuvette is squeezed (reduced in size) and an air jet is directed against the liquid surface formed in the cuvette adjacent the junction of the liquid surface with the wall of the cuvette to create a vortex to produce thorough mixing of the contents of the cuvette and substantially prevent any splashing of the liquid contents.

31 Claims, 4 Drawing Sheets

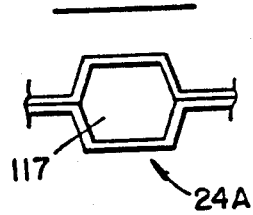
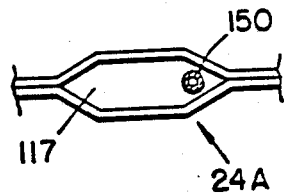
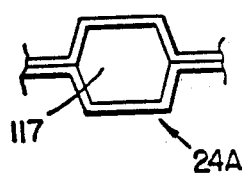
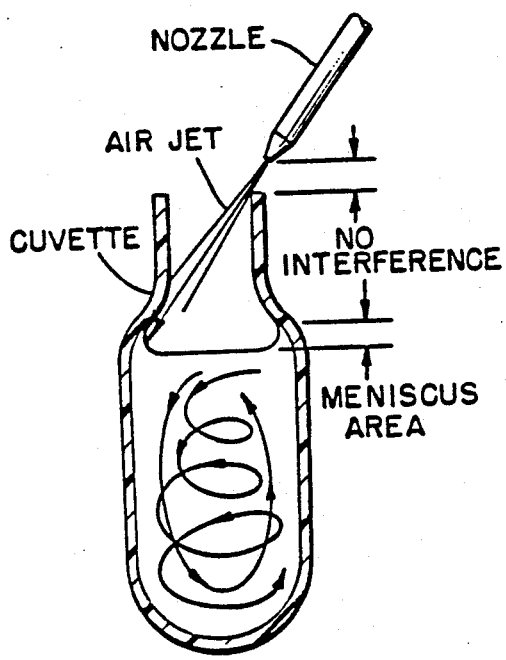
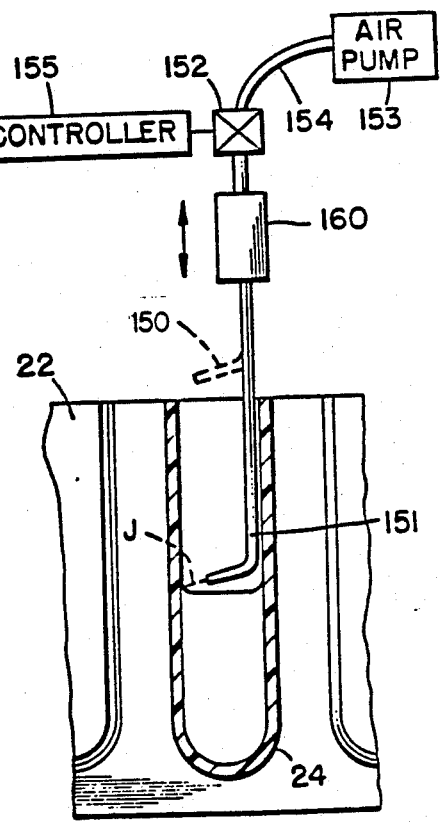

CLINICAL ANALYSIS METHODS AND SYSTEMS

BACKGROUND OF THE INVENTION

I. Field of the Invention

This invention relates generally to the mixing of materials and to the analysis of the results of such mixing. In particular, the invention relates to improved methods, apparatus and systems for mixing materials and the analysis of the results of such improved mixing. The present invention is particularly useful in automated chemistry analyzers for determining the presence and levels of one or more selected constituents in relatively small biological liquid samples.

II. Description of the Prior Art

Numerous automated clinical analyzers are known and widely used in hospital clinical laboratories. An example of such an analyzer is the multi-channel type analyzer.

A multi-channel analyzer is one in which a series of different tests are performed simultaneously by the analyzer, and in parallel with one another. Such an analyzer can be best visualized as a series of batch analyzers operating in parallel wherein each channel performs a single analysis test. The multi-channel type analyzer generally utilizes a liquid reagent to react with the particular constituent being tested in the sample and a photo-optical system to read the optical absorbence of the sample which corresponds to the level of the constituent in the sample.

Although this type of automated analyzer has received wide acceptance in the clinical laboratory certain drawbacks are associated with its use. For example, although the multi-channel type analyzer is reliable due to its simplicity, cost effective for large number of samples and has a relatively high test throughput rate, it is limited in the sense that it can only be effectively utilized to perform a single constituent analysis at a time on a relatively large number of samples. In addition, such analyzers are not capable of performing emergency "stat" tests due to their relatively long and complex set up time and their inherent inability to economically analyze a single test sample.

A further significant disadvantage found is that although they can simultaneously perform tests for multiple constituents on the same sample, generally all of these tests must be performed for every sample whether desired or not. This results in a waste of both sample material and the reagents used in the unnecessary tests. Furthermore, due to the fact that multiple discrete and dedicated channels are utilized in such an instrument, there is significant duplication of numerous components which adds to the complexity and expense of the overall instrument.

An automated single track clinical analyzer which avoids the above-described drawbacks is described in commonly owned U.S. Pat. No. 4,528,159, issued July 9, 1985, entitled, "Automated Analysis Instrument System". By using a unique photo-optical system, described in commonly owned U.S. Pat. No. 4,477,190, issued Oct. 16, 1984, entitled, "Multichannel Spectrophotometer", greater flexibility of analysis at each analysis station is achieved. This is because the photo-optical system employs fiber optic bundles or similar light guides to transmit variable wavelengths of light to each analysis station from a single light source.

The single track analyzer utilizes a disposable cuvette belt formed form thin plastic film and defining a series of discrete reaction compartments (cuvettes) which are transported in line ahead through the instrument. Such a cuvette belt is described in commonly owned U.S. Patent Application Ser. No. 284,842, filed July 20, 1981 entitled, "Cuvette System For Automated Chemical Analyzers", now abandoned. This belt provides handling flexibility and avoids the cross-contamination associated with flow-through cuvettes as well as avoiding the washing required for reusable cuvettes.

The earlier clinical analyzers discussed above employed liquid reagent, and mixing of the reagent with the diluent prior to addition of the biological sample. One method of achieving such mixing was by shooting a stream of the liquid reagent into the cuvette so as to produce a vortex-type mixing process. A preferred feature of the analyzer disclosed in U.S. Pat. No. 4,528,159 is that it is adapted to utilize dry particulate reagents, preferably in tablet form, which are dispensed into the cuvettes from a rotating carousel which can hold a large number of doses. A preferred embodiment of tablet dispenser is described in commonly owned U.S. Pat. No. 4,405,060, issued Sept. 20, 1983, entitled, "Tablet Dispensing Device". In order to effect dissolution of the dry particulate reagent within the diluent prior to addition of the biological sample, the reagent and diluent are mixed by ultrasonic means.

An improvement in the reliability and controllability of the analysis of liquid samples, particularly liquid biological samples, is achieved by mixing the contents of the cuvette after addition of the sample by directing an air jet at an acute angle against the surface of the liquid in the cuvette. Particularly good mixing is obtained when the air jet is directed at the liquid surface adjacent its junction with the wall of the cuvette. The optimum point of contact of the air jet with the liquid surface is the meniscus formed at the junction between the liquid surface and the wall of the cuvette.

The combination of directing the air jet against the liquid surface adjacent its junction with the wall of the cuvette and directing it at an acute angle to the surface producing a horizontal component has the beneficial effect of creating a vortex which produces a thorough mixing of the contents of the cuvette. Thus, a whirling or circular motion is induced in the contents tending to form a cavity of vacuum in the center and to draw the materials at the edge towards the center thus providing an effective mixing action. Particularly where the air jet hits the contents of the cuvette in the meniscus region, the contents tend to be raised up the wall of the cuvette opposite where the air jet hits the contents creating a particularly effective vortex producing very good mixing of the sample with the diluent and reagent. Thus, a particulate reagent will become totally suspended within the diluent and the sample optimizing the reaction of the sample therewith. This improved mixing technique is described in commonly owned U.S. Patent Application Ser. No. 848,851, filed Apr. 4, 1986, a continuation of Ser. No. 575,924, filed Feb. 1, 1984, now abandoned entitled, "Clinical Analysis Systems and Methods", the disclosure of which is hereby incorporated by reference in its entirety herein.

SUMMARY OF THE INVENTION

In several of the prior clinical analyzers as described above, the reagent and diluent are mixed in the cuvette prior to the addition of the liquid biological sample, either by shooting the reagent into the diluent to form a vortex in the case of a liquid reagent or by ultrasonic mixing in the case of the dry particulate reagent. The present invention seeks to improve over both of these techniques.

It has been found in accordance with the present invention that improved reliability and controllability of the analysis of the samples is achieved by providing an improved swirl path during mixing and at the same time minimizing splashing of the sample.

It is therefore an object of the present invention to provide an improved method, apparatus and system for mixing materials and for analyzing the results of such mixing which are substantially devoid of many disadvantages of the prior art and which also represent a substantial improvement over the prior art.

Another object of the present invention is to provide an improved swirl path during mixing.

Still another object of the present invention is to minimize splash of the liquid while providing an improved swirl path. Thus splashing of the contents out of the cuvette leading to intercuvette contamination can be avoided.

Still another object of the present invention is to provide a system for mixing materials which will allow keeping the mixing pressure at very high levels to achieve excellent mixing without causing any of the problems associated with splashing.

The foregoing objects and others are accomplished in accordance with the present invention by providing an improved method, apparatus and system for mixing materials, particularly biological liquid samples, and for analyzing the mixed materials wherein the materials are placed in a cuvette and an air jet is used to agitate the materials sufficiently to cause the materials to mix. It is a critical step in accordance with the present invention that during the air jet mixing process, the top (opening) of the cuvette is squeezed to reconfigure it and reduce the size of the opening.

In an automated system, the cuvette is partially filled to a predetermined liquid level and then advanced into alignment stationarily beneath a fixed nozzle so that the latter is aimed at the junction of liquid surface and cuvette wall at which time the top (opening) portion of the cuvette is squeezed or reduced in size. The angle of the air jet nozzle should ideally be as far as possible from the vertical providing maximum horizontal components of the air jet upon the liquid. The angle is determined by the diameter of the cuvette, the liquid level in the cuvette, which is itself controlled by the requirement to avoid splashing of the contents out of the cuvette, and the position of the nozzle over the mouth of the cuvette.

While it is preferred, particularly in an automated process, that the air jet nozzle direct air into the cuvette from outside the cuvette, it is within the spirit and scope of this invention to direct the air jet from inside the cuvette and aimed at the liquid surface from a position above the liquid surface. While requiring insertion and removal of the nozzle into and out of the cuvette (either by lowering and raising the nozzle or by raising and lowering the cuvette) this does have the advantage that the nozzle can be angled more closely to the horizontal without spilling of the contents. Thus, the nozzle may be inclined at an angle of between about 0 degrees to about 90 degrees to the horizontal, with the preferred angle of between about 8 and 15 degrees. Depending upon the height of the nozzle above the liquid surface, it may become contaminated by the liquid during agitation in which case the nozzle should be cleaned with diluent between mixing operations. It will be noted that in this embodiment as well as in that described above, the nozzle is arranged above the liquid surface and is therefore non-invasive of the liquid.

The present invention permits thorough mixing of the reagent, diluent and sample which enhances reliability and controllability of the test(s) of the sample. The mixing process occurs in a very fast time frame. Intercuvette contamination is avoided by reducing the size opening of the top of the cuvette and controlling the mixing action so that splashing of material out of the cuvette is prevented. There is no physical contact between the nozzle and the contents of the cuvette, and by having the nozzle arranged outside the cuvette, contamination of the nozzle is avoided and there is no need to move any component into the cuvette to effect the mixing, thus maximizing throughput in an automated process.

While the unique air jet mixing system of this invention has particular application to the mixing of biological samples in clinical analyzers as described above, it also has general application to the mixing of liquids with one or more other liquids or solids.

DESCRIPTION OF THE DRAWINGS

Other features and advantages of the present invention will become apparent from the following description taken in conjunction with the accompanying drawings wherein:

FIG. 6 is a top plan view of a cuvette prior to the top opening thereof being squeezed during the mixing process;

FIG. 7 is a top plan view of the cuvette shown in FIG. 6 as the top opening is squeezed by the apparatus illustrated in FIG. 5;

FIG. 8 is a top plan view of the cuvette shown in FIG. 7 after it has passed through the apparatus shown in FIG. 5;

FIG. 9 is a schematic side elevation view showing the mixing action produced when the apparatus in accordance with the present invention is in use; and FIG. 10 is a schematic side elevation view of a second embodiment of mixing apparatus suitable for use in the clinical analyzer of FIG. 1.

DESCRIPTION OF THE PREFERRED EMBODIMENTS

Figure 1:
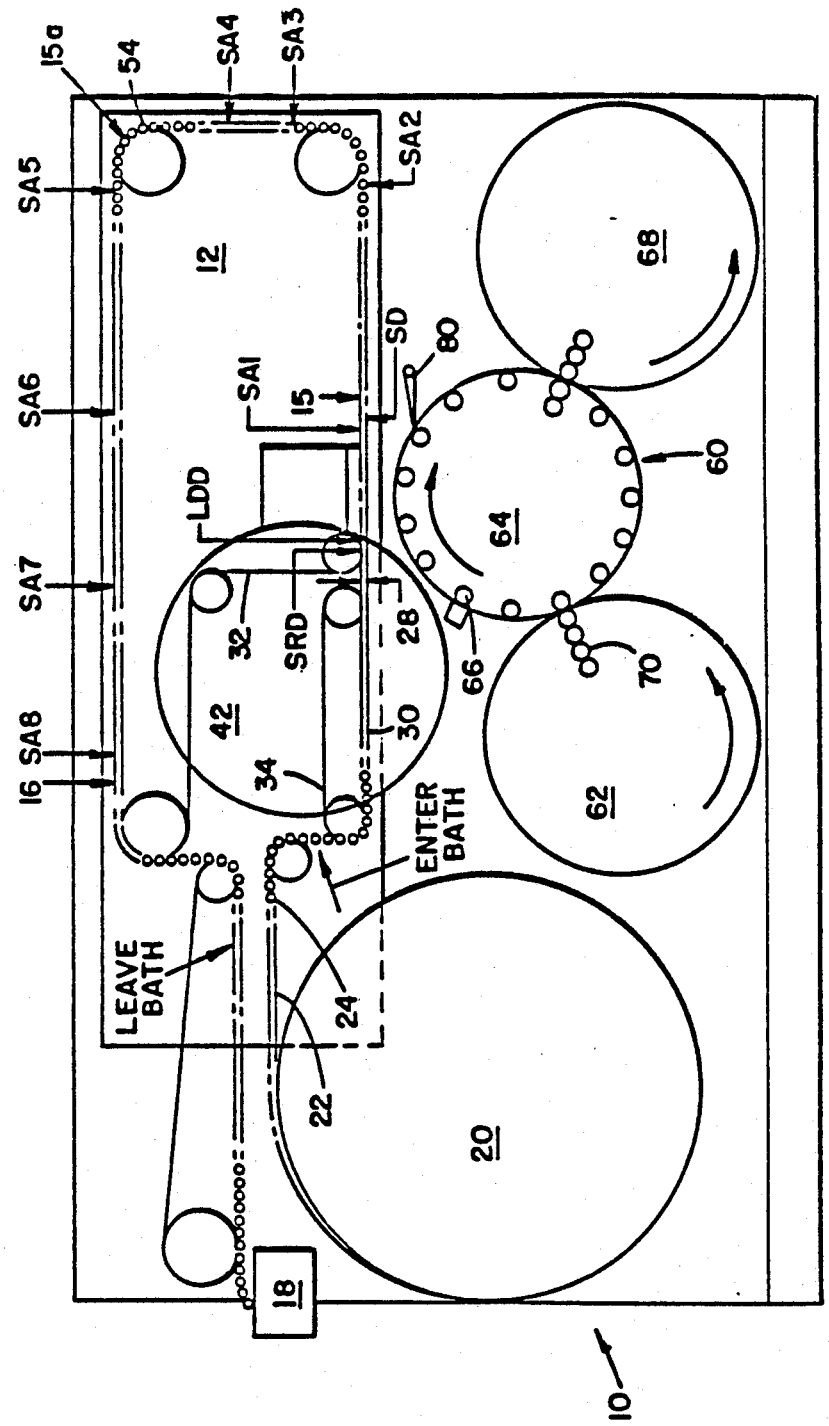
FIG. 1 is a schematic plan view of an automatic clinical analyzer that can incorporate the features of the present invention.
Figure 2:
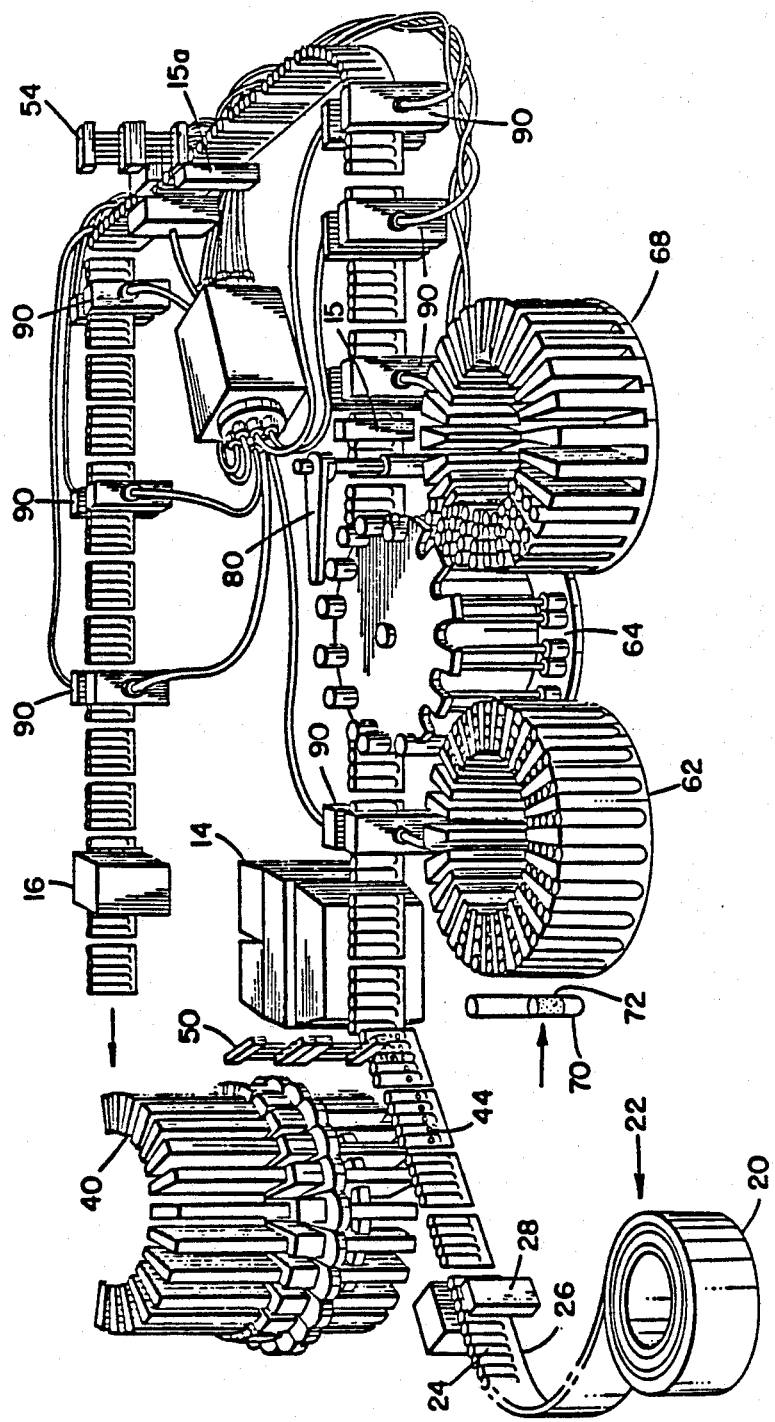
FIG. 2 is a partial perspective view of the automated clinical analyzer shown in FIG. 1.

FIGS. 1 and 2 illustrate, as one example, an automated clinical analyzer 10 generally described in the aforesaid U.S. Patent Application Ser. No. 848,851 that can incorporate the features of the present invention. More particularly, the analyzer is a Paramax Analytical System as manufactured by Baxter Healthcare Corporation. The analyzer 10 is particularly adapted for the testing of constituents in biological fluids, such as blood samples.

The analyzer comprises a series of processing stations past which strips of disposable reaction cuvettes are indexed or advanced. The cuvettes 24 are supplied from a supply reel 20 as a continuous cuvette belt 22 and are indexed through the analyzer by tractor conveyor 30 which engages a row of index holes in the cuvette belt. The cuvettes are indexed in turn past the following stations: a belt cutter 28 for dividing the belt into sections; a tabletted reagent dispenser 40; a diluent and liquid reagent dispenser 50; an ultrasonic mixing horn 14; a sample dispenser 80 for dispensing biological samples delivered by a transfer carousel 64; an air jet mixing apparatus 15 including an apparatus for squeezing the top (opening) of the cuvette during the air jet mixing process (shown and described hereinbelow), according to the invention for mixing the sample with the reagent and diluent in the cuvettes and substantially preventing splashing of the sample; eight photometric read stations 90; a further reagent dispenser 54; a further air jet mixing apparatus 15a for mixing the sample and the further reagent; a cuvette sealer 16 and a cuvette collection station 18.

During their passage through the analyzer, the cuvettes are carried in a water bath 12 maintained at a constant temperature. The cuvette belt 22 is preferably constructed and made in the manner more fully described in aforesaid U.S. Patent Application Ser. No. 284,842.

Figure 3:
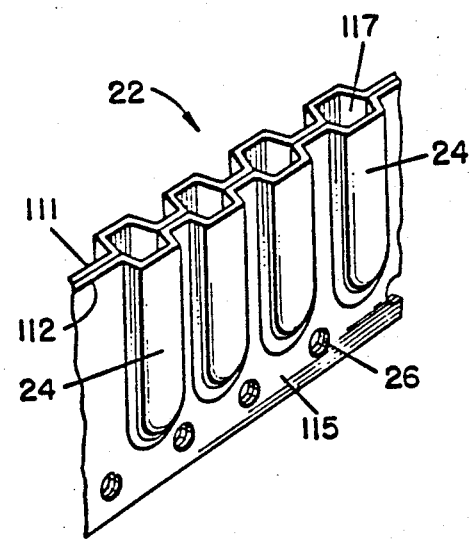
FIG. 3 is a perspective view of a cuvette belt for use in the clinical analyzer of FIG. 1.

As shown in FIG. 3, the belt 22 comprises two strips 111, 112 of transparent flexible plastic material which are moulded and sealed together to form a series of discrete, side-by-side parallel compartments (cuvettes) 24 separated by webs 115. The cuvettes are formed of a plastic material which is sufficiently flexible to enable the top to be squeezed so that the tops (openings) thereof are partially closed during the mixing process and then return to their normal top (opening) position when the squeezing action is stopped.

The compartments are closed at one end and have a top or opening or open mouth 117 at the other end so as to receive and retain fluid therein. For example, the cuvettes can be in the order of size so as to be capable of holding about 500 microliters of fluid. The flat web material 115 between the vessels 24 includes a transport strip portion extending alongside the closed ends thereof which is formed with indexing perforations or holes 26. These perforations are engaged by the tractor transport 30 of the analyzer 10 for conveying the cuvettes therethrough and maintaining a precise alignment of the optical paths through the cuvettes with the photo-optical examining system at the analysis stations 90.

The transport 30 comprises a single continuous guide and support track extending through the analyzer having a main tractor belt 32 which engages the indexing holes 26 in the cuvette belt 22 and advances the cuvettes through the instrument at a predetermined rate of advance. A short loading belt 34 threads the cuvette belt 22 into engagement with the main tractor belt 32. The transport 30 advances or indexes the cuvettes through the analyzer 10 in steps corresponding to the spacing between cuvettes (the pitch of the belt) with the cuvettes being stopped and held stationary for a dwell period between each advance. Each step may suitably correspond to a time interval of 5 seconds with a 4 second dwell time between each indexing advance of the cuvettes.

The reagent tablet dispenser carousel 42 comprises a circular array of tabletted reagent dispensers 40 and can be rotated to bring the correct solid reagent dispenser to solid reagent dispensing point "SRD" to drop a single reagent tablet 44 into a cuvette 24. As illustrated, the carousel 42 accommodates thirty-two reagent tablet dispensers 40. It is rotated under microprocessor control to bring the correct tablet dispenser to the dispensing point for each cuvette. The dispensers 40 are detachable and can be loaded randomly. An automatic flagging system indicates when a dispenser is low in tablets.

The diluent and/or liquid reagent dispenser 50 is located adjacent to carousel 42 for adding sufficient diluent 52 for reagent tablet 44 dissolution and/or for dispensing a liquid reagent into the reaction vessel (cuvette) 24 at point "LDD".

The ultrasonic horn 14 acts on the cuvette contents for a sufficient length of time; for example, 45 seconds, to totally dissolve the reagent tablets.

A sample loading and transfer carousel assembly 60 is located downstream of the reagent and diluent dispensers. This carousel assembly comprises a loading carousel 62 into which patient samples 70 are randomly loaded. It also includes a transfer carousel 64 which accepts the patient samples 70 from loading carousel 62, identifies the patient sample by means of a bar code reader 66 which reads a bar code label 72 placed on the patient sample container and continuously feeds the patient samples into the system. Finally, an unloading carousel 68 receives the patient samples 70 after testing and stores them in an organized manner in the event that they must later be located and retrieved.

The loading carousel 62 permits continuous random loading of up to 96 patient samples. The transfer carousel 64 continuously feeds patient samples into the system for maximum throughput. Standard collection tubes or microsample tubes may be accommodated thus allowing utilization of the same containers in which the sample is collected; for example, in the case of blood samples, the "Vacutainer" tube which is commonly used to draw the serum specimen.

Sample dispenser 80 for dispensing samples into the cuvettes 24 at point "SD" is located adjacent to transfer carousel 64. This sampler is designed to aspirate about 2 to 20 microliters of patient sample 70 from its container in the transfer carousel and dispense it into a cuvette 24 during the four second dwell period while the cuvette is aligned with the sampler.

The air jet mixing apparatus 15 (and 15a) directs an air jet, preferably at an acute angle, against the liquid surface in the cuvette adjacent its junction with the cuvette wall to create a vortex. The vortex produces a thorough mixing of the sample with the reagent and diluent in accordance with the teachings of the system as described in the aforesaid U.S. Patent Application Ser. No. 848,851. In a preferred embodiment, the apparatus has a fixed, inclined nozzle 150 and the cuvettes 24 are aligned in position beneath the nozzle and the air jet is switched on only during the dwell period when the cuvette is stationery. In order to ensure that the air jet correctly strikes the liquid surface, the liquid level is closely controlled.

Eight photometric analysis stations 90 are located at points "SA1" through "SA8" along the cuvette track 30. The station "SA1" is arranged following the ultrasonic horn 14 for verifying proper reagent dispensing and dissolution. The second reagent dispenser 54 permits further reaction of the sample to be obtained following initial testing and is shown arranged between analysis stations "SA4" and "SA5". It could be located between any of the analysis stations "SA2" to "SA8". This capacity for optional reagent additions or triggered reaction capability gives added analytical versatility for multiple reagent test situations.

The further air jet mixing apparatus 15a provides for thorough remixing of the cuvette contents following addition of further reagent at station 54.

The cuvette sealer 16 seals the tops of the tested cuvettes for convenient clean disposal of completed samples at the cuvette disposal location where they are neatly collected into a lined disposal bin.

The microprocessor control system of the clinical analyzer, which suitably has a 280 processing unit, controls all the operating units thereof in accordance with sample and test information inputted at a suitable operator interface keyboard. In accordance with the desired test results, quantities of a single sample may be dispensed into one or more cuvettes either alone or in combination with any one or more of the solid and liquid reagents and diluents, and examined at any one or more of the analysis stations 90. Test results are displayed on a screen and can be printed out.

Turning now specifically to the features of the present invention, there is shown in FIGS. 4-8 embodiments of a mixing apparatus together with an apparatus for reducing the top (opening) of the cuvette during the mixing process, according to the present invention, suitable for use on the above described automated clinical analyzer 10 at mixing station 15.

Figure 4:
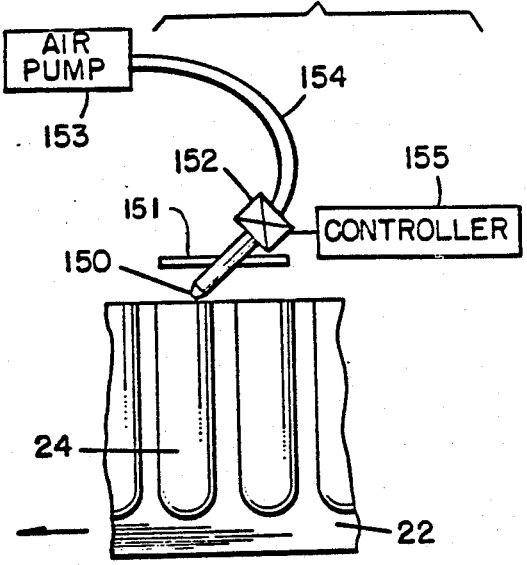
FIG. 4 is a schematic side elevation of a mixing apparatus.

FIG. 4 shows an embodiment of mixing apparatus 15 comprising a nozzle 150 arranged above the path of the cuvettes 24 with which the cuvettes are in turn aligned so that the nozzle is directed preferably at an acute angle at the junction between the surface of the liquid in the cuvette and the wall of the cuvette. The nozzle 150 is fixed in position. In order to insure that the air jet J produced thereby is properly coordinated with the liquid surface in the cuvette so that it strikes the surface at the junction thereof with the cuvette wall, the quantities of reagent, diluent and sample are closely controlled so that the liquid in all the cuvettes is at a constant preset level. (One exception to this is where the sample is dispensed into a cuvette alone for sample blanking and mixing is not required.)

The nozzle 150 is mounted on a frame 151 so that its orifice is just above the tops of the cuvettes with sufficient clearance to avoid interference with the cuvettes as they are advanced. It may, for example, be about 0.7 mm above the tops of the cuvettes. While the nozzle is fixed in position during use, the frame 151 may incorporate means for adjusting the angle of the nozzle either manually or automatically during set-up or between runs. A valve 152 is provided for controlling the supply of air to the nozzle 150 from an air supply 153 to which it is connected by an air line 154. Operation of the valve 152 is by means of a controller 155 connected to the analyzer's microprocessor.

As explained above, the cuvettes are indexed stepwise through the analyzer along track 30 and each cuvette is positioned stationarily in alignment beneath the orifice of the nozzle 150 during the dwell period between advancing steps. Activation of the air jet J is limited to this dwell period so that the cuvettes are stationary during mixing.

Figure 5:
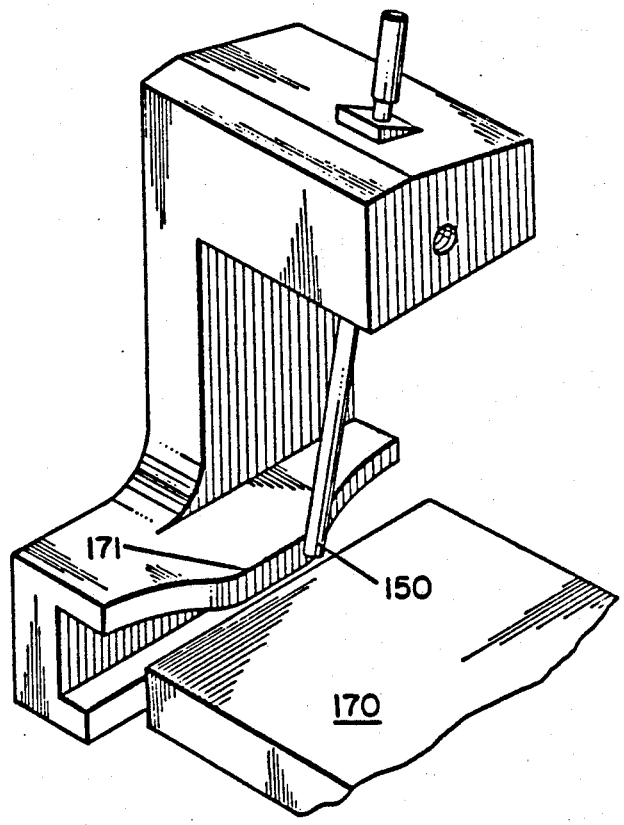
FIG. 5 is a partial perspective view showing the relationship of a mixing apparatus and apparatus for reducing the opening of the top of a cuvette during mixing in accordance with the features of the present invention.

A critical feature of the present invention is illustrated in FIGS. 5 through 8. As shown in FIG. 5, an air jet mixing apparatus, such as air jet mixing apparatus 15, includes a means to squeeze the top (opening) of the cuvette to reconfigure it during the application of the air jet mixer process. This is accomplished by guiding one edge of the cuvette by a fixed rail 170 and squeezing the other side of the cuvette towards it by a bracket 171 which acts as an obstacle in the path of the cuvette as it passes into and through the air jet mixing station. The net effect of this apparatus is that when the cuvette has been positioned at the air jet mixer for mixing the material therein, and is in a stationary position ready for mixing, the top (opening) portion of the cuvette is squeezed partially closed and held in that position during the mixing process.

The squeezing or reconfiguring of the top (opening) or mouth of the cuvette minimizes the opening to provide a better swirl path during the mixing process and also minimizes splash of the liquid contents. It has been found in accordance with the present invention that best results are achieved when the cuvette top (opening) is squeezed (closed up) to about 75 percent of the original top (opening) size.

The overall (before, during and after) effect on the top (opening) of a single cuvette 24A is best illustrated in FIGS. 6 through 8. The cuvette 24A illustrated in FIG. 6 shows the top (opening) of a cuvette just prior to entering the air jet mixer station. In FIG. 7 there is illustrated the top (opening) of cuvette 24A as it looks squeezed between fixed rail 170 and bracket 171 (See FIG. 5) with the nozzle 150 of the air jet mixer in place ready for mixing. FIG. 8 illustrates the cuvette 24A top (opening) after passing through the fixed rail and bracket squeezing apparatus.

By directing the air jet J at an acute angle at the junction of the liquid surface in the cuvette with the partially closed top (opening) portion with the cuvette wall, preferably so that the air jet hits the meniscus at this junction, a vortex is created which produces a thorough mixing of the contents of the cuvette. This mixing is such that even a reagent which is particularly immissible in the diluent becomes totally suspended within the diluent and the reaction between the reagent and the sample is more complete and rapidly achieved.

FIG. 9 shows a representative pattern of such mixing within the cuvette by the air jet J. However, the exact pattern of mixing taken by the material may be any suitable one. By ensuring that the air jet hits the liquid surface in the meniscus area, very good mixing within the material is achieved. During such mixing, it is seen that the materials climb the wall of the cuvette opposite the point where the air jet strikes the liquid surface. This is depicted by the dotted swirling action behind the air jet at the right-hand side of the cuvette in FIG. 9.

By squeezing (closing) of the top (opening) of the cuvette as shown, all of the advantages of the present invention are achieved. The use of an air jet to mix the contents of the cuvette in the manner described has been found to work surprisingly well considering the relatively small amount of fluid being mixed and the relatively small confines of the cuvette in which the mixing has to take place. Specific details of how the air jet can be arranged with regard to the cuvette described herein or other cuvette the various angles of the inclination of the jet, jet pressures, activation times, etc. are described in detail in the aforementioned U.S. patent application, Ser. No. 848,851, all of which is incorporated by reference herein.

In operation, the cuvettes 24 are advanced in turn into position beneath the nozzle 150 in alignment therewith which is closely controlled by the tractor belt 32, and the top (opening) of each cuvette when in position for mixing is squeezed closed as shown by FIGS. 5 and 7. The microprocessor, which has already closely controlled the quantities of materials dispensed into the cuvette to the preset liquid level, then directs the air jet at the meniscus at the junction between the liquid surface and the cuvette wall to create a vortex which produces a thorough mixing of the contents of the cuvette. At the end of the dwell period, the air jet is switched off, and the cuvette belt is advanced to bring the next cuvette into stationary position beneath the nozzle when the cuvette top (opening) squeezing step and mixing process is repeated.

In the embodiment described above, the air jet nozzle 150 is non-invasive of the cuvette, thus maximizing throughput. However, in a modification as shown in FIG. 10, the nozzle is inserted into the cuvette during the squeezing and mixing process as described above. This has the effect of limiting throughput and may result in contamination of the nozzle which can be dealt with by flushing the nozzle with diluent between mixing operations. However, it does produce a system in which the angle of inclination of the nozzle is not limited by the geometry of the cuvette so that it can be inclined more nearly to the horizontal thus desirably maximizing the horizontal component of the air jet. In this embodiment, the nozzle 150 has a dog-leg bend in it and is mounted on an elevator mechanism schematically represented at 160 by which it can be raised and lowered between a lowered, operative position as shown in solid outline and a raised, inoperative position as shown in dotted outline for cuvette indexing. With this arrangement the air jet angle can be reduced to as little as 8 degrees to the liquid surface (horizontal). An angle of between about 8 degrees and about 15 degrees to the horizontal is preferred. As in the previous embodiment, the air jet is directed at the junction between the liquid surface and the cuvette wall.

It should be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. In a method of mixing materials, at least one of which is a liquid, in a cuvette wherein an air jet is used to agitate the materials sufficiently to cause the materials to mix, the improvement which comprises reducing the opening of the cuvette during the air jet mixing process.

2. A method in accordance with claim 1 wherein the opening of the cuvette is reduced by squeezing the top of the cuvette opening.

3. A method in accordance with claim 2 wherein said opening of said cuvette is reduced up to about 75 percent of the original opening size.

4. A method in accordance with claim 1 wherein said air jet is directed at an acute angle against the liquid surface in said cuvette adjacent its junction with the wall of said cuvette.

5. A method in accordance with claim 4 including directing said air jet against the meniscus formed at the junction of the liquid surface and the wall of said cuvette.

6. A method in accordance with claim 1 wherein said cuvette is maintained stationary during said mixing.

7. A method in accordance with claim 1 including directing said air jet from a nozzle arranged outside said cuvette.

8. A method in accordance with claim 1 including the step of inserting a nozzle from which said air jet is directed into said cuvette to a position above the surface of said liquid and directing said air jet against the liquid surface from said nozzle.

9. A method in accordance with claim 1 wherein said materials comprise a liquid and particulate material.

10. A method according to claim 9 including directing said air jet against the meniscus formed at the junction of the liquid surface and the wall of said cuvette from a fixed nozzle arranged outside said cuvette while maintaining said cuvette stationary.

11. A method in accordance with claim 1 wherein said materials comprise a biological sample and a reagent.

12. A method in accordance with claim 1 wherein said materials comprise a biological sample, a reagent and a diluent.

13. A method in accordance with claim 1 further comprising the step of analyzing the contents of said cuvette following said mixing step.

14. In a method of analyzing materials including a biological sample and a liquid wherein the sample and liquid are dispensed into a cuvette, an air jet is used to mix all materials, and the contents of the cuvette following the mixing are analyzed, the improvement which comprises reducing the size of the opening of the cuvette during the air jet mixing process.

15. A method in accordance with claim 14 wherein said opening of said cuvette is reduced up to about 75 percent of the original opening size.

16. A method in accordance with claim 14 wherein said materials include a diluent, reagent and liquid biological sample which are mixed in said cuvette.

17. A method in accordance with claim 16 in which said reagent is a dry particulate reagent.

18. A method in accordance with claim 16 in which the contents following said mixing are analyzed a plurality of times at intervals.

19. A method in accordance with claim 14 wherein said air jet is directed at an acute angle against the liquid surface in said cuvette adjacent its junction with the wall of said cuvette.

20. A method in accordance with claim 14 wherein the analysis is by photometry.

21. A method in accordance with claim 14 including advancing said cuvette beneath a fixed nozzle from which said air jet is directed and maintaining said cuvette stationary while directing said air jet against said liquid surface from outside said cuvette.

22. A method according to claim 14 including advancing said cuvette into alignment beneath a nozzle from which said air jet is directed, lowering the nozzle into said cuvette above the liquid surface and maintaining said cuvette stationary while directing said air jet against said liquid surface from said nozzle.

23. Apparatus for mixing materials, at least one of which is a liquid, including means for dispensing said materials into a cuvette through its opening to form a liquid surface in the cuvette, a nozzle means for directing an air jet against the liquid surface so formed in the cuvette so as to agitate said materials sufficiently to cause mixing of said materials, means for reducing the size of the opening of the cuvette during the air jet mixing process, and means for advancing said cuvette from said dispensing means to align it with said nozzle means.

24. An apparatus according to claim 23 wherein said reducing means squeezes the top of said cuvette opening.

25. An apparatus according to claim 23 wherein said reducing means reduces said cuvette opening up to about 75 percent of the original opening size.

26. An apparatus according to claim 23 wherein said nozzle means directs said air jet at an acute angle against said liquid surface adjacent its junction with the wall of said cuvette.

27. Apparatus according to claim 26 in which said cuvette is partially filled by said dispensing means to a predetermined level and said cuvette is so aligned with said nozzle that said air jet is directed against the meniscus formed at the junction of the liquid surface and a wall of the cuvette.

28. An apparatus according to claim 23 wherein said reducing means comprises two surfaces between which the portion of said cuvette with said opening passes.

29. Apparatus for mixing liquid and particulate materials in a cuvette, comprising:
 means for dispensing at least one liquid and at least one particulate material into the cuvette through its opening to form a liquid surface in the cuvette bound by the wall of the cuvette at a predetermined level in the cuvette;
 a fixed air jet nozzle for directing an air jet against the liquid surface to mix said materials;
 means for reducing the opening of the cuvette during the air jet mixing process; and
 means for advancing the cuvette from the dispensing means into stationary position beneath said air jet nozzle in alignment with said nozzle.

30. Apparatus for mixing liquid and particulate materials in a cuvette comprising:
 means for dispensing at least one liquid and at least one particulate material into the cuvette through its opening to partially fill the cuvette and form a liquid surface in the cuvette bound by the wall of the cuvette;
 an air jet nozzle;
 means for advancing the cuvette from the dispensing means into stationary position beneath said air jet nozzle;
 means for lowering said air jet nozzle into the cuvette to position it a predetermined height above said liquid surface in the cuvette, said nozzle to direct an air jet against said liquid surface in the cuvette to mix said materials, and for raising said air jet nozzle out of said cuvette following said mixing; and
 means for reducing the opening of the cuvette during the air jet mixing process.

31. An apparatus for analyzing liquid biological samples comprising the following means and means for advancing a cuvette between said means in order:
 (a) means for dispensing a reagent and a diluent into the cuvette through its opening and for mixing the reagent and the diluent to disperse the reagent in the diluent;
 (b) means for adding a liquid biological sample to the cuvette, the quantities of said reagent, diluent and sample dispensed being controlled so that together they partially fill the cuvette and define a liquid surface bound by the wall of the cuvette;
 (c) nozzle means for directing an air jet against the liquid surface so as to cause mixing of the contents of the cuvette to facilitate reactions of the sample;
 (d) means for reducing the opening of the cuvette during the air jet mixing process; and
 (e) means for analyzing the reaction of the reagent with the sample following said mixing.

* * * * *